United States Patent [19]

Murai et al.

[11] 4,182,767

[45] Jan. 8, 1980

[54] ANTIHYPERGLYCEMIC N-ALKYL-3,4,5-TRIHYDROXY-2-PIPERIDINE METHANOL

[75] Inventors: Hiromu Murai, Otsu; Hiroshi Enomoto, Nagaokakyo; Yoshiaki Aoyagi, Kyoto; Yoshiaki Yoshikuni, Kameoka; Masahiro Yagi, Kusatsu; Ichiro Shirahase, Kyoto, all of Japan

[73] Assignee: Nippon Shinyaku Co., Ltd., Japan

[21] Appl. No.: 906,233

[22] Filed: May 10, 1978

[30] Foreign Application Priority Data

Jun. 25, 1977 [JP] Japan .................. 52-075936

[51] Int. Cl.$^2$ .................. A61K 31/445; C07D 211/46
[52] U.S. Cl. .................................... 424/267; 546/242
[58] Field of Search .................. 260/293.9; 424/267; 546/242

[56] References Cited

U.S. PATENT DOCUMENTS 4,065,562  12/1977  Ohata et al. .................. 424/267

OTHER PUBLICATIONS

Inouye, S. et al., *J. Antibiotics, Ser. A,* 19(6), 288 (1966).
Saeki, H. et al., *Chem. Pharm. Bull.,* 16(5), 962 (1968).

*Primary Examiner*—Alan L. Rotman
*Assistant Examiner*—Richard A. Schwartz
*Attorney, Agent, or Firm*—Jacobs & Jacobs

[57] ABSTRACT

2-Hydroxymethyl-3,4,5-trihydroxy-N-alkylpiperidines and their acid addition salts are antihyperglycemic agents. A typical example is 2-hydroxymethyl-3,4,5-trihydroxy-N-methylpiperidine.

7 Claims, No Drawings

ANTIHYPERGLYCEMIC N-ALKYL-3,4,5-TRIHYDROXY-2-PIPERIDINE METHANOL

DETAILED DESCRIPTION

This invention relates to novel N-alkylpiperidine derivatives of the formula, and acid addition salts thereof:

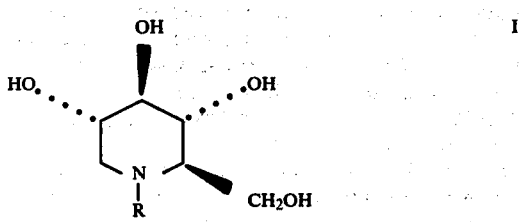

wherein R is alkyl of 1 to 4 carbon atoms.

The compounds of Formula I and their salts are novel substances which have not been described in the literature. These substances are antihyperglycemic agents and medicinally useful. The property manifests itself through inhibition of an increase of blood sugar in humans and other animals.

The present invention also pertains to the physiologically acceptable nontoxic acid addition salts of these basic compounds. Such salts include those derived from organic and inorganic acids such as, without limitation, hydrochloric acid, hydrobomic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

A number of procedures are available for synthesizing the contemplated compounds of this invention. One of these involves alkylation of the corresponding N-nor-compound of Formula II wherein R' is hydrogen:

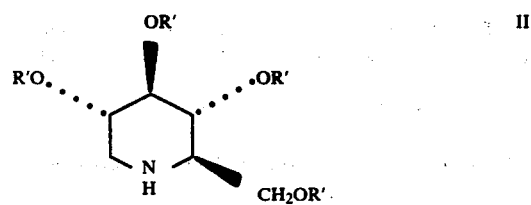

This alkylation can be effected by various alternative procedures. For example compounds of Formula II can be treated with an alkyl halide, preferably in the presence of an acid acceptor. A compound of Formula II can also be N-acylated and the product then reduced to the N-alkyl compound. Reductive alkylation involving the use of a carbonyl compound can also be employed. It is advantageous in the latter two instances to start with a compound of Formula II having suitably protected hydroxyl groups, i.e. R' is benzyl, benzoyl, acetyl, or the like, with the N-alkylation reaction being followed by removal of the protective groups by conventional techniques.

The compounds of the present invention are generally administered orally in any of the usual pharmaceutical forms. These include solid and liquid oral unit dosage forms such as tablets, capsules, powders, suspensions, solutions, syrups and the like, including sustained release preparations. The term unit dosage form as used in this specification and the claims refer to physically discrete units to be administered in single or multiple dosage to animals, each unit containing a predetermined quantity of the piperidine derivative in association with the required diluent, carrier or vehicle. The quantity of the piperidine derivative is that calculated to produce the desired antihyperglycemic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the piperidine compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The midicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Suspensions can be formulated by dispersing the compound in a nontoxic vehicle in which it is insoluble.

The antihyperglycemic activity can be conveniently observed in well known and widely employed laboratory models, as for example the depression of blood sugar levels in glucose loaded rats. The compounds are administered in the conventional manner to humans and other animals, in each case carefully titrating the dose to the age, condition and response of the recipient.

The following examples are intended to further describe the method by which the compounds of this invention are produced. It should, however, be understood that the invention is not limited to the substances specifically mentioned in those examples.

EXAMPLE 1

A mixture of 7 ml of aqueous formalin, 15 ml of formic acid, 1.5 g of 2-hydroxymethyl-3,4,5-trihydroxypiperidine, m.p. 204°–205°, $[\alpha]_D^{25}+45°$ ($H_2O$), is heated under reflux for 20 hours. The reaction mixture is then concentrated to dryness under reduced pressure, the residue is dissolved in water and the insolubles are removed by filtration. The filtrate is passed over ion exchange resin column (Dowex 50 W×4). The column is rinsed with water and the absorved material is eluted with 0.28% aqueous ammonia. The eluate is concentrated to dryness under reduced pressure and the crystalline residue is recrystallized from ethanol to yield 2-hydroxymethyl-3,4,5-trihydroxy-N-methylpiperidine, m.p. 142°–143°, $[\alpha]_D^{24}+15.5°$ ($H_2O$), yield 1.2 g. Treatment with an equimolar amount of p-toluenesulfonic acid gives the corresponding p-toluenesulfonate which, in turn, is recrystallized from methanol. m.p. 198°–199°, $[\alpha]_D^{24}+12.2°$ (methanol).

EXAMPLE 2

In 10 ml of dimethylformamide are dissolved 500 mg of the starting material of Example 1. This is followed by the addition of 1.0 g of anhydrous potassium carbonate and 3 ml of methyl iodide. The mixture is stirred at room temperature for 24 hours. The reaction mixture is diluted with water and passed over ion exchange resin column (Dowex 50 W×4). The column is rinsed with water and the absorbed material is eluted with 0.28% aqueous ammonia. The eluate is concentrated to dryness under reduced pressure, extracted with hot methanol, and after insolubles are filtered off, p-toluenesulfonic acid is added. The resulting crystals, identical with the material of Example 1, are collected by filtration and recrystallized from methanol. m.p. 198°–199°; yield 0.24 g.

EXAMPLE 3

In 50 ml of dimethylformamide is dissolved 1.0 g of 2-benzyloxymethyl-3,4,5-tribenzyloxylpiperidine, m.p. 44°–47°. This is followed by the addition of 3.0 g of anhydrous potassium carbonate and 2.0 g of propyl bromide. The mixture is stirred under heating at 60°±3° for 12 hours, after which it is diluted with water and extracted with benzene. The extract as such is dissolved in a mixture of 10 ml of 47% hydrobromic acid and 7 ml of acetic acid, followed by heating at 100° C. for one hour. After cooling, 100 ml of methanol are added into the reaction mixture, and the solution is hydrogenated over 300 mg of 5% palladium-charcoal. After this catalytic reduction has been completed, the catalyst is removed by filtration and the filtrate is concentrated to dryness under reduced pressure. The residue is dissolved in water and the solution is passed over ion exchange resin column (Dowex 50 W×4). The eluate is distilled under reduced pressure to recover 205 mg of 2-hydroxymethyl-3,4,5-trihydroxy-N-propylpiperidine as colorless oil. This product is converted to the p-toluenesulfonate salt which, after recrystallization from isopropyl alcohol, melts at 208°–211°. $[\alpha]_D^{24}+0.4°$ (methanol). By substituting ethyl bromide for propyl bromide, the corresponding N-ethyl compound is obtained.

EXAMPLE 4

In 20 ml of pyridine is dissolved 1.0 g of the hydrochloride salt of the starting material of Example 3, m.p. 185°–189°. Following addition of 1.1 g of isobutyryl chloride, the solution is held at room temperature for 24 hours. The reaction mixture is then concentrated to dryness under reduced pressure, the residue is extracted with ether and the ethereal layer is washed with dilute alkali and acid. The ether is then removed by distillation to yield 1.1 g of 2-benzyloxymethyl-3,4,5-tribenzyloxy-N-isobutyrylpiperidine as colorless oil. IR spectrum: $\nu_{max}^{film}$ 1670 cm$^{-1}$. This isobutyryl derivative, without further purification, is reduced in 20 ml of tetrahydrofuran with 500 mg lithium aluminum hydride with heating and stirring for 2 hours. The excess reactant and reaction mixture is decomposed, and concentrated in the usual fashion and the colorless oil obtained from this mixture is dissolved in a mixture of 10 ml of 47% hydrobromic acid and 10 ml of acetic acid. This mixture is heated at 100° C. for one hour, diluted with 100 ml of methanol, and catalytically hydrogenated over 300 mg of 5% palladium charcoal. Following the work-up described in Example 3, there is obtained 2-hydroxymethyl-3,4,5-trihydroxy-N-isobutylpiperidine as an oil which is converted to p-toluenesulfonate which is recrystallized from isopropanol. m.p. 192°–194°, $[\alpha]_D^{25}-8.3°$ (methanol), yield 0.46 g.

What is claimed is:

1. A compound selected from the group consisting of an N-alkylpiperidine of the formula:

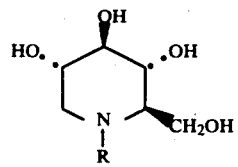

wherein R is alkyl of 1 to 4 carbon atoms, and the pharmaceutically acceptable nontoxic acid addition salts thereof.

2. The compound according to claim 1 wherein R is methyl.

3. The compound according to claim 1 wherein R is ethyl.

4. The compound according to claim 1 wherein R is propyl.

5. The compound according to claim 1 wherein R is isobutyl.

6. The method of effecting an antihyperglycemic effect in humans and other animals which comprises administering thereto an antihyperglycemically effective amount of a compound according to claim 1.

7. A pharmaceutical composition comprising an antihyperglycemically effective amount of a compound according to claim 1 in combination with a pharmaceutically acceptable carrier.

* * * * *